(12) United States Patent
McHardy et al.

(10) Patent No.: US 7,129,263 B2
(45) Date of Patent: Oct. 31, 2006

(54) PREPARATION OF 3-AZABICYCLO [3.1.0] HEXANE DERIVATIVES

(76) Inventors: Stanton Furst McHardy, 525 Hill Farm Rd., Coventry, RI (US) 02816; John Anthony Ragan, 1 Lark La., Gales Ferry, CT (US) 06335; Derek Lawrence Tickner, 14 Longview Ave., Waterford, CT (US) 06385; Brian Clement Vanderplas, 6 Craig Rd., Old Lyme, CT (US) 06371; Jotham Wadsworth Coe, 8 Bush Hill Dr., Niantic, CT (US) 06340

( * ) Notice: Subject to any disclaimer, the term of this patent is extended or adjusted under 35 U.S.C. 154(b) by 33 days.

(21) Appl. No.: 10/966,712

(22) Filed: Oct. 15, 2004

(65) Prior Publication Data

US 2005/0113437 A1    May 26, 2005

Related U.S. Application Data

(60) Provisional application No. 60/511,889, filed on Oct. 16, 2003.

(51) Int. Cl.
*A61K 31/403* (2006.01)
*C07D 209/52* (2006.01)
(52) U.S. Cl. ..................... 514/412; 548/515
(58) Field of Classification Search ............... 514/412; 548/515

See application file for complete search history.

(56) References Cited

U.S. PATENT DOCUMENTS

2003/0087898 A1* 5/2003 McHardy et al. ........ 514/224.2

* cited by examiner

*Primary Examiner*—Kamal A. Saeed
*Assistant Examiner*—Michael P. Barker

(57) ABSTRACT

This present invention relates to a new and improved reductive amination process for the preparation of 3-azabicyclo[3.1.0]hexane derivatives and pharmaceutical compositions comprising such derivatives. The invention particularly relates to using such derivatives to treat certain disorders and conditions, including, for example, irritable bowel syndrome, drug addiction or dependency, alcohol addiction or dependency, depression, and eating disorders.

11 Claims, No Drawings

PREPARATION OF 3-AZABICYCLO [3.1.0] HEXANE DERIVATIVES

FIELD OF THE INVENTION

This present invention relates to a new and improved reductive amination process for the preparation of 3-azabicyclo[3.1.0]hexane derivatives and pharmaceutical compositions comprising such derivatives. The invention particularly relates to using such derivatives to treat certain disorders and conditions, including, for example, irritable bowel syndrome, drug addiction or dependency, alcohol addiction or dependency, depression, and eating disorders.

BACKGROUND OF THE INVENTION

Compounds that bind to opiate receptors (e.g. mu, kappa and delta opioid receptors) are likely to be useful in the treatment of diseases modulated by opiate receptors, for example irritable bowel syndrome; constipation; nausea; vomiting; and pruritic dermatoses, such as allergic dermatitis and atopy in animals and humans. Compounds that bind to opiate receptors have also been indicated in the treatment of eating disorders, opiate overdoses, depression, smoking and alcohol addiction and dependence, sexual dysfunction, shock, stroke, spinal damage and head trauma.

It is furthermore beneficial to obtain drugs that bind to opioid receptors which are not substrates of the enzyme CYP2D6. The presence of CYP2D6 enzyme among the human population is variable, and therefore it is easier to develop dosage schemes for a drug that are more generally applicable to a human population if the drug is not metabolized by CYP2D6.

Certain 4-arylpiperidine-based compounds are disclosed in European patent applications EP 287339, EP 506468 and EP 506478 as opioid antagonists. In addition, International Patent Application WO 95/15327 discloses azabicycloalkane derivatives useful as neuroleptic agents. 3-Azabicyclo [3.1.0]hexane derivatives useful as opioid receptor antagonists are also disclosed in WO 00/39089.

The synthesis, composition, and methods of use of certain 3-azabicyclo[3.1.0]hexane derivatives are disclosed in U.S. Pat. No. 6,313,312 and United States Patent Application 2003/0087898. The present invention provides an alternative route to these compounds with improved yield.

The aforementioned patents and patent applications are incorporated herein by reference therein in their entirety.

SUMMARY OF THE INVENTION

According to the invention there is provided a process for the preparation of 3-azabicyclo[3.1.0.]hexane derivatives having the formula:

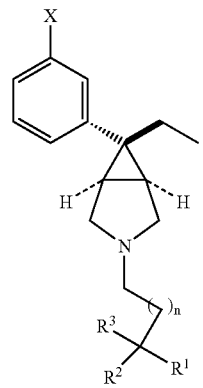

I wherein X is halogen, —OH, —CN, —$C_1$ to $C_4$ alkyl substituted with one to three halogen atom, —$NH_2$, —NH($C_1$–$C_4$ alkyl), —N($C_1$–$C_4$ alkyl)($C_1$–$C_4$ alkyl), —C(=O) $NH_2$, —C(=O)NH($C_1$–$C_4$alkyl), —C(=O)N($C_1$–$C_4$ alkyl) ($C_1$–$C_4$ alkyl), —NHS(=O)$_2$H, or —NHS(=O)$_2R^4$;

$R^1$ and $R^2$ are, with the carbon to which they are attached, connected to form a $C_3$–$C_7$ cycloalkyl or a 4–7 membered heterocycloalkyl comprising from one to three hetero moities selected from O, S, —C(=O), and N; and wherein said cycloalkyl or heterocycloalkyl optionally contains one or two double bonds; and wherein said cycloalkyl or heterocycloalkyl is optionally fused or attached to a $C_6$–$C_{14}$ aryl or 5–14 membered heteroaryl group;

$R^3$ is $C_1$–$C_4$ alkyl which may optionally contain one or two unsaturated bonds, —OH, —CN, —$NO_2$, —$OC_1$–$C_4$ alkyl, —$NH_2$ amide or alkyl substituted amide and n is one or zero;

$R^4$ is selected from $C_1$–$C_4$ alkyl, -($C_1$–$C_4$ alkylene)—O— ($C_1$–$C_4$ alkyl), 4-(1-methylimidazole), -($C_1$–$C_4$ alkylene)— $NH_2$, -($C_1$–$C_4$ alkylene)—NH($C_1$–$C_4$ alkyl), -($C_1$–$C_4$ alkylene)—N($C_1$–$C_4$ alkyl)($C_1$–$C_4$ alkyl);

comprising reacting a compound of formula

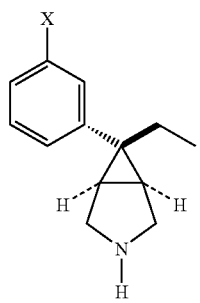

II with a compound of formula

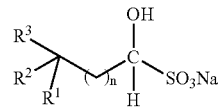

III in the presence of a reducing agent and an organic solvent; wherein $R^1$, $R^2$, $R^3$, and n are as defined above.

In a preferred embodiment of the present invention $R^1$ and $R^2$ are, with the carbon to which they are attached, connected to form a $C_5$ cycloalkyl group. In another preferred embodiment n is zero and $R^3$ is —OH.

In one embodiment of the present invention, the compound of formula III is the addition product (adduct) of aqueous sodium bisulfite and an organic aldehyde of formula IV wherein the adduct exists in a solution equilibrium with sodium bisulfite and the aldehyde.

In another embodiment of the present invention, the aldehyde-bisulfite adduct in the presence of a base is substantially dissociated into sodium bisulfite and the corresponding aldehyde IV.

In another embodiment the solvent is 2-methyl-tetrahydrofuran and the base is aqueous sodium hydroxide in sufficient amount to elevate the pH of the reaction mixture to a pH of at least 9.0.

In yet another embodiment of the present invention the reducing agent is sodium triacetoxyborohydride.

In another embodiment the organic solvent is a mixture of N-methylpyrrolidone (NMP) and a $C_5$–$C_{10}$ hydrocarbon, preferably cyclohexane.

In another embodiment the compound of formula III is selected from the group consisting of:
Hydroxy-(2-hydroxyindan-2-yl)-methanesulfonic acid, sodium salt;
Hydroxy-[cis-1-hydroxy-3-(4-methoxy-phenyl)-cyclobutyl]-methanesulfonic acid, sodium salt;
Hydroxy-[cis-1-hydroxy-3-phenyl-cyclobutyl]-methanesulfonic acid, sodium salt;
Hydroxy-[cis-1-hydroxy-3-(4-fluoro-phenyl)-cyclobutyl]-methanesulfonic acid, sodium salt; and
Hydroxy-[cis-1-hydroxy-3-(4-bromo-phenyl)-cyclobutyl]-methanesulfonic acid, sodium salt;

In another embodiment the compound of formula I is selected from the group consisting of:
Exo-N-{3-[6-ethyl-3-(2-hydroxy-indan-2-ylmethyl)-3-aza-bicyclo[3.1.0]hex-6-yl]-phenyl}-methanesulfonamide;
Exo-{3-[6-ethyl-3-(cis-1-hydroxy-3-phenyl-cyclobutylmethyl)-3-aza-bicyclo[3.1.0]hex-6-yl]-phenyl}-propanesulfonamide;
Exo-N-{3-[6-ethyl-3-(2-hydroxy-indan-2-ylmethyl)-3-aza-bicyclo[3.1.0]hex-6-yl]-phenyl}-propanesulfonamide;
Exo-{3-[6-ethyl-3-(cis-1-hydroxy-3-(4-bromo-phenyl)-cyclobutylmethyl)-3-aza-bicyclo[3.1.0]hex-6-yl]-phenyl}-methanesulfonamide;
Exo-N-{3-[6-ethyl-3-(2-hydroxy-indan-2-ylmethyl)-3-aza-bicyclo[3.1.0]hex-6-yl]-phenyl}-(2-methoxyethane)sulfonamide;
Thiophene-2-carboxylic acid (3-fluoro-4-morpholin-4-yl-phenyl)-[Exo-3-(2-hydroxy-indan-2-ylmethyl)-3-aza-bicyclo[3.1.0]hex-6-ylmethyl]-amide; and
Exo-N-{3-[6-ethyl-3-(2-hydroxy-indan-2-ylmethyl)-3-aza-bicyclo[3.1.0]hex-6-yl]-phenyl}-ethanesulfonamide
and their pharmaceutically acceptable salts and prodrugs.

In another embodiment the compounds of formula I are used in the treatment of irritable bowel syndrome, drug addiction, alcohol addiction, depression and eating disorders.

DETAILED DESCRIPTION OF THE INVENTION

The present invention provides a new process for the preparation of selected 3-azabicyclo[3.1.0]hexane derivatives (formula I) by the reductive amination of aldehyde-bisulfite adducts of formula III with the corresponding heterocyclic amine of formula II. The synthesis of compounds of formula II is disclosed in U.S. Pat. No. 6,313,312.

In accordance with the present invention, compounds of formula I above may be prepared by the reductive amination illustrated below:

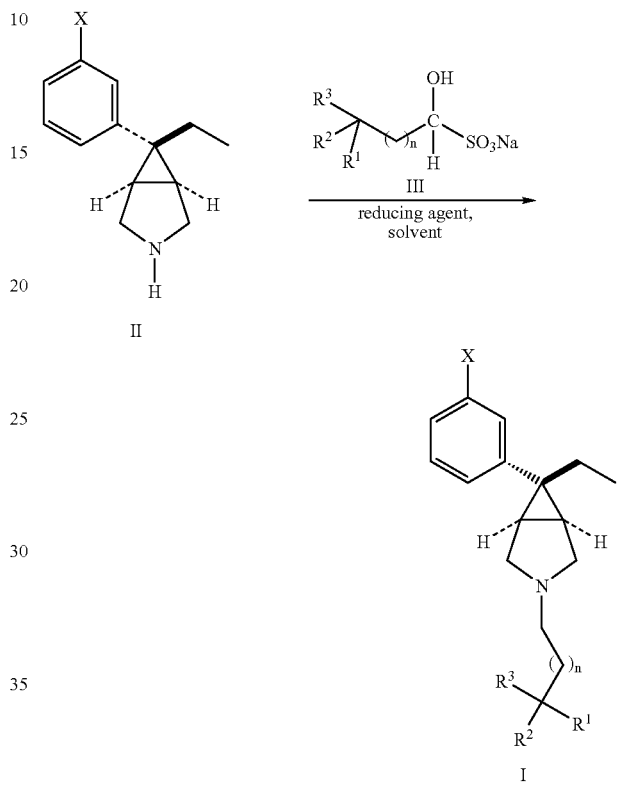

wherein X, n and $R^1$ through $R^3$ are as defined above.

As illustrated above, treatment of an amino compound of formula II with the sodium bisulfite adduct of an appropriately substituted aldehyde of formula III and a reducing agent in an organic solvent produces the corresponding compound of formula I.

Reductive aminations are discussed generally in a "Advanced Organic Chemistry", 3$^{rd}$ Ed., J. March, pp. 798–800, John Wiley & Sons, 1985, New York.

The present invention provides an alternative route to compounds of formula I in high purity and yield. Prior attempts to prepare compounds of formula I as disclosed in U.S. Application No. 2003/0087898, utilized the free aldehyde (IV) in the reductive amination reaction described above.

In the present invention, the aldehyde-bisulfite adducts III are expected to give increased product yield by providing the aldehyde in a more stable form which is less prone to side-reactions such as, for example, dimer formation. For purposes of the present invention the term adduct refers to a compound which is the addition product of an aldehyde and sodium bisulfite.

In a preferred embodiment of the present invention, the reducing agent is sodium triacetoxyborohydride, and the organic solvent is 2-methyltetrahydrofuran or a mixture of N-methylpyrrolidone and cyclohexane.

Compounds of formula III are addition products (adducts) resulting from the reaction of aqueous sodium bisulfite and the corresponding aldehyde (IV) as illustrated below:

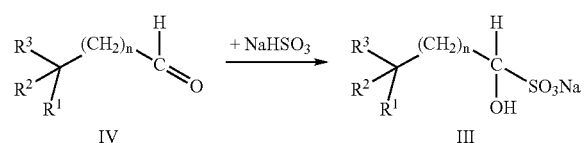

The adducts of formula III are isolated prior to treatment with compounds of formula II.

In one embodiment, the amine II may be treated with the adduct (III) in the form of an equilibrium mixture of aldehyde IV and sodium bisulfite. Alternatively, the amine II is treated with the adduct in the presence of a base resulting in substantial dissociation of the adduct into the aldehyde and sodium bisulfite.

The present inventors have discovered that the use of aldehyde-bisulfite adducts in the reductive-amination reaction leading to compounds of formula I provides significantly higher yield as compared to the unmodified aldehyde. For example, when the α carbon contains a hydroxyl group ($R^3$ is —OH and n is zero), the corresponding aldehyde is unstable and highly reactive tending to form unwanted dimers and oligomers. The present invention overcomes this problem by providing a derivative of the aldehyde in the form of the bisulfite adduct which exhibits highly selective reactivity and is less prone to undergo undesirable side reactions.

Compounds of formula I are useful in treating mammals, including a human, in need thereof a disorder or condition selected from irritable bowel syndrome; constipation; nausea; vomiting; pruritic dermatoses, including allergic dermatitis and contact dermatitis; psoriasis; eczema; an insect bite; an eating disorder, including anorexia, bulimia, and obesity; depression, smoking addiction; drug addiction, including alcohol addiction, amphetamine addiction, cocaine addiction and addiction to an opiate, for example morphine, opium, or heroine; an opiate overdose; a sexual dysfunction, including erectile dysfunction and impotence; stroke; head trauma; traumatic brain injury; spinal damage; Parkinson's disease; Alzheimer's disease, age-related cognitive decline; and Attention Deficit and Hyperactivity Disorder; which composition comprises an amount of a compound of formula I effective in treating said disorder or condition and a pharmaceutically acceptable carrier.

The terms "treatment", "treating", and the like, refers to reversing, alleviating, or inhibiting the progress of the disorder or condition to which such term applies, or one or more symptoms of such disorder or condition. As used herein, these terms also encompass, depending on the condition of the patient, preventing the onset of a disorder or condition, or of symptoms associated with a disorder or condition, including reducing the severity of a disorder or condition or symptoms associated therewith prior to affliction with said disorder or condition. Thus, "treatment", as used herein, can refer to administration of a compound of the invention to a subject that is not at the time of administration afflicted with the disorder or condition. "Treating" thus also encompasses preventing the recurrence of a disorder or condition or of symptoms associated therewith.

"Mammal", as used herein, and unless otherwise indicated, means any mammal. The term "mammal" includes, for example and without limitation, dogs, cats, and humans.

References herein to disorders and conditions "mediated by an opioid receptor or receptors" indicate disorders or conditions that are caused at least in part by binding of the endogenous ligands to an opioid receptor, for example endogenous ligand binding to a mu, kappa, and/or delta opioid receptor. Examples of disorders and conditions that are mediated by an opioid receptor or receptors include, but are not limited to, irritable bowel syndrome, eating disorders, sexual dysfunction, depression, smoking and drug addictions, as well as the other specific disorders and conditions recited above.

The stereochemistry of compounds of formula I synthesized according to the methods described above can be determined using standard spectroscopic methods. Isolation of the exo diastereomer of a compound of formula I from an exo/endo mixture can be accomplished using standard separation methods know to those of ordinary skill in the art, for example crystallization or chromatographic methods.

Pharmaceutically acceptable salts of a compound of formula I can be prepared in a conventional manner by treating a solution or suspension of the corresponding free base or acid with one chemical equivalent of a pharmaceutically acceptable acid or base. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids. Illustrative bases are sodium, potassium, and calcium.

A compound of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a compound of formula I or a pharmaceutically acceptable salt thereof can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

A compound of formula I or a pharmaceutically acceptable salt thereof can be administered orally, transdermally (e.g., through the use of a patch), parenterally (e.g. intravenously), rectally, topically, or by inhalation. In general, the daily dosage for treating a disorder or condition as described herein using a compound of formula I will be about from about 0.01 to about 100 mg per kg, preferably from about 0.1 to about 10 mg per kg, of the body weight of the animal to be treated. As an example, a compound of the formula I, or a pharmaceutically acceptable salt thereof, can be administered for treatment to an adult human of average weight (about 70 kg) in a dose ranging from about 0.5 mg up to about 10 g per day, preferably from about 10 mg to about 1 g per day, in single or divided (i.e., multiple) portions. Variations based on the aforementioned dosage ranges may be made by a physician of ordinary skill taking into account known considerations such as the weight, age, and condition of the animal being treated, the severity of the affliction, and the particular route of administration chosen.

Affinity of a compound for the delta opioid receptor can be assessed using binding of the delta opioid receptor ligand [3H]-naltrindole to NG108-15 neuroblastoma-glioma cells according to modification of the protocol described in Law et al. (Law, P. Y., Koehler, J. E. and Loh, H. H., "Comparison of Opiate Inhibition of Adenylate Cyclase Activity in Neuroblastoma N18TG2 and Neuroblastoma X Glioma NG108-15 Hybrid Cell Lines", *Molecular Pharmacology*, 21: 483–491 (1982)). Law et al. is incorporated herein in its entirety by reference. Affinity of a compound for the kappa opioid receptor can be assessed using binding of [$^3$H]-bremazocine to kappa receptors as described in Robson, L. E., et al., "Opioid Binding Sites of the Kappa-type in Guinea-pig Cerebellum", *Neuroscience (Oxford)*, 12(2): 621–627 (1984). Robson et al. is incorporated herein it its entirey by reference. For assessment of a compound for mu opioid receptor activity, the mu receptor ligand [$^3$H]-DAMGO (Perkin Elmer Life Sciences, Boston, Mass.; specific activity 55 Ci/mmol, 1.5 nM) is used with rat forebrain tissue. Briefly, the binding is initiated with the addition of a crude membrane preparation of rat forebrain tissue to 96-well polypropylene plates containing the radioligand [$^3$H]-DAMGO and test compound, and are incubated for about 90 minutes at about 25° C. The assay is terminated by rapid filtration with 50 mM Tris HCl pH 7.4 onto Wallac Filtermat B and counted on a Betaplate reader (Wallac).

The data generated can be analyzed using IC$_{50}$ analysis software in Graphpad Prism. Ki values can be calculated using Graphpad Prism according to the following formula:

$$Ki=IC_{50}/1+[^3H \text{ ligand}]/K_D$$

where IC$_{50}$ is the concentration at which 50% of the $^3$H ligand is displaced by the test compound and K$_D$ is the dissociation constant for the $^3$H ligand at the receptor site.

EXAMPLE 1

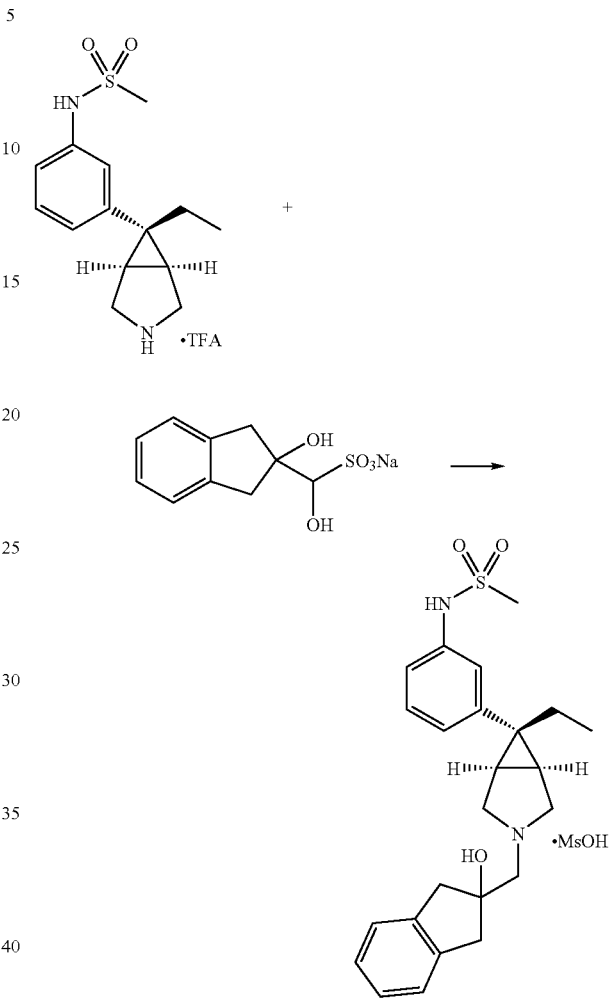

Reductive amination, General Method A: Exo-N-{3-[6-ethyl-3-(2-hydroxy-indan-2-ylmethyl)-3-aza-bicyclo[3.1.0]hex-6-yl]-phenyl}-methanesulfonamide.

Exo-N-{3-[6-ethyl-3-aza-bicyclo[3.1.0]hex-6-yl]-phenyl}-methanesulfonamide (5.00 g, 12.7 mmol) and hydroxy-(2-hydroxyindan-2-yl)-methanesulfonic acid, sodium salt (7.43 g, 50% by weight with NaHSO$_3$, 14.0 mmol) were combined in 50 mL N-methylpyrrolidone. Cyclohexane (25 mL) was added, and the slurry heated in a 110° C. oil bath. The mixture was distilled through a short path condenser to remove the water-cyclohexane azeotrope, collecting ca. 20 mL. The resulting solution was maintained at 105° C. for 20 min, then cooled to room temperature. Sodium triacetoxyborohydre (4.03 g, 19.0 mmol) was then added in a single portion. After 20 min, LC/MS analysis indicated complete conversion to the desired product. The reaction was quenched by careful addition of 10 mL water, diluted with 10% aq Na$_2$CO$_3$ and brine, then extracted with two 50 mL portions of EtOAc. The organic extracts were combined and concentrated to provide 5.3 g of product (free base) as a brown oil. Addition of methanesulfonic acid in 2:1 EtOAc-EtOH provided the mesylate salt in 54% overall yield (3.58 g).

EXAMPLE 2

Reductive amination, General Method B: Exo-N-{3-[6-ethyl-3-(2-hydroxy-indan-2-ylmethyl)-3-aza-bicyclo[3.1.0]hex-6-yl]-phenyl}-methanesulfonamide.

Exo-N-{3-[6-ethyl-3-aza-bicyclo[3.1.0]hex-6-yl]-phenyl}-methanesulfonamide (12.0 g, 30.4 mmol) and (2-hydroxyindan-2-yl)-carboxaldehyde (10.8 g, 66.7 mmol, as a solution in 150 mL 2-Me-THF)** were combined. The solution was heated to distill off water as its azeotrope with 2-Me-THF, collecting ca. 100 mL of distillate. The solution was cooled to room temperature, then treated portionwise with 12.9 g Na(OAc)$_3$BH (12.9 g, 61 mmol) and stirred overnight. The reaction was quenched by addition of 100 mL 20% Na$_2$CO$_3$ (aq), and the phases separated. The aqueous phase was washed with water, then concentrated to an oil. Ethyl acetate (65 mL) and ethanol (32 mL) were added, and methanesulfonic acid (2.0 mL, 31 mmol) was added dropwise over 5 min. The resulting solids were stirred overnight, then cooled to 0° C. for 30 min. Filtration, rinsing with cold ethyl acetate, provided 11.3 g pale yellow solids (71% yield).

**Bisulfite adduct break: The bisulfite adduct (hydroxy-(2-hydroxyindan-2-yl)-methanesulfonic acid, sodium salt) is partitioned between 8 volumes (mL/g) water and 10 volumes 2-Me-THF. Three volumes of 1 N NaOH are then slowly added, to provide an aqueous pH of 9–10. The phases are separated, and the organic phase washed with two 5 volume portions of 20% Na$_2$CO$_3$ (aq). The 2-Me-THF solution is used directly in the above process (an aliquot is concentrated to provide the concentration of aldehyde).

EXAMPLE 3

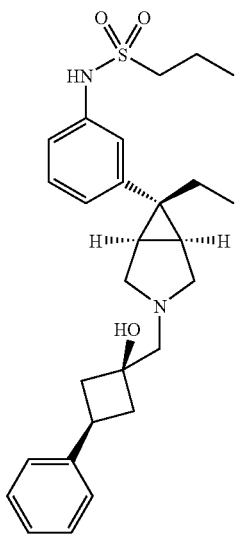

Exo-{3-[6-ethyl-3-(cis-1-hydroxy-3-phenyl-cyclobutylmethyl)-3-aza-bicyclo[3.1.0]hex-6-yl]-phenyl}-propanesulfonamide:

Following general Method B, Exo-{3-[6-ethyl1-3-aza-bicyclo[3.1.0]hex-6-yl]-phenyl}-propanesulfonamide hydrochloride I (50 mg, 0.16 mmol) and hydroxy-[cis-1-hydroxy-3-phenyl-cyclobutyl]-methanesulfonic acid, sodium salt (100 mg, 0.32 mmol) were coupled to provide the title compound.

EXAMPLE 4

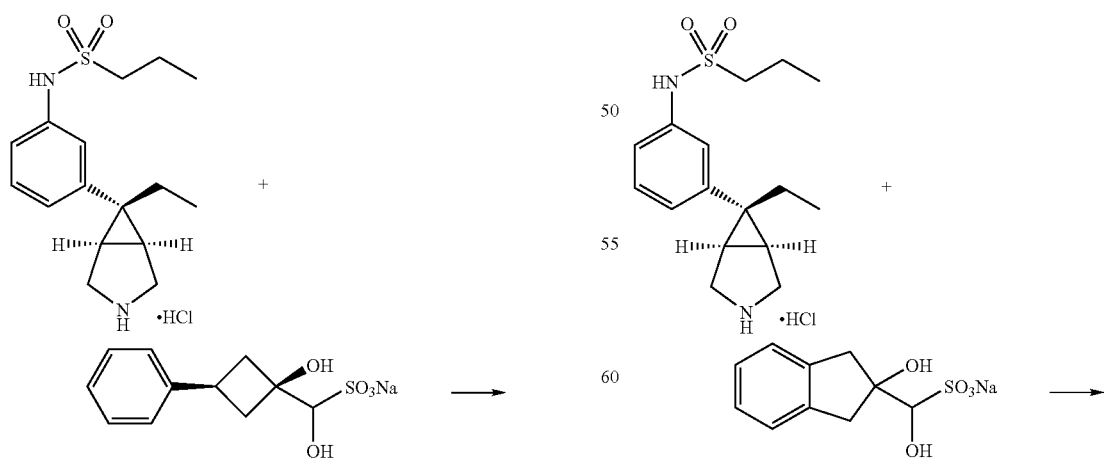

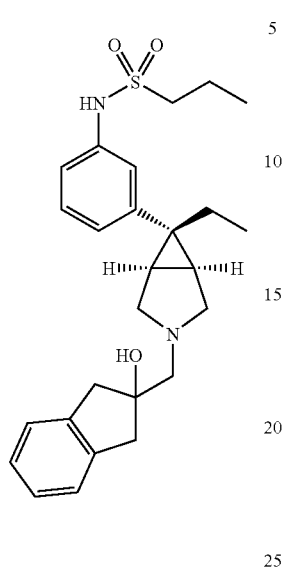

Exo-N-{3-[6-ethyl-3-(2-hydroxy-indan-2-ylmethyl)-3-aza-bicyclo[3.1.0]hex-6-yl]-phenyl}-propanesulfonamide:

Following General Method B, Exo-N-{3-[6-ethyl-3-aza-bicyclo[3.1.0]hex-6-yl]-phenyl}-propanesulfonamide hydrochloride (215 mg, 0.32 mmol) and hydroxy-(2-hydroxyindan-2-yl)-methanesulfonic acid, sodium salt (215 mg, 0.80 mmol) were coupled to provide the title compound.

EXAMPLE 5

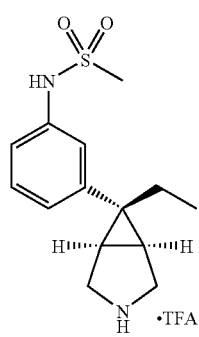

+

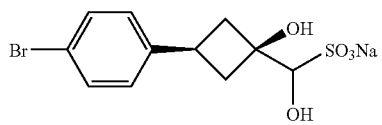

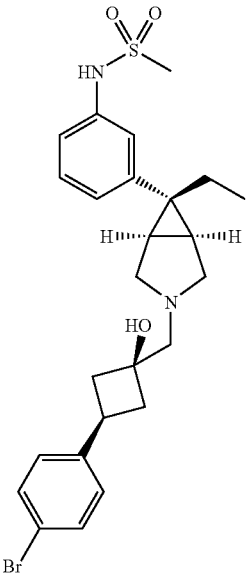

Exo-{3-[6-ethyl-3-(cis-1-hydroxy-3-(4-bromo-phenyl)-cyclobutylmethyl)-3-aza-bicyclo[3.1.0]hex-6-yl]-phenyl}-methanesulfonamide:

Following General Method B, Exo-{3-[6-ethyl-3-aza-bicyclo[3.1.0]hex-6-yl]-phenyl}-methanesulfonamide trifluoroacetate (100 mg, 0.25 mmol) and hydroxy-[cis-1-hydroxy-3-(4-bromo-phenyl)-cyclobutyl]-methanesulfonic acid, sodium salt (183 mg, 0.51 mmol) were coupled to provide the title compound.

EXAMPLE 6

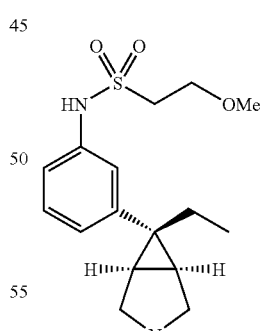

+

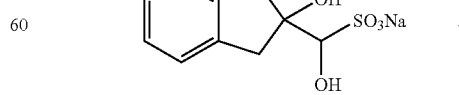

-continued

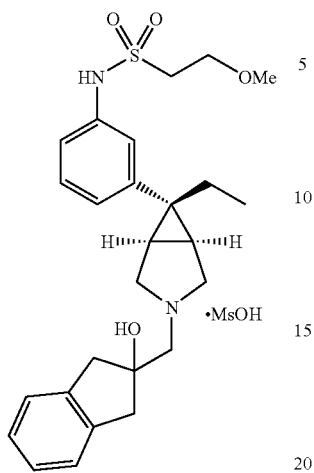

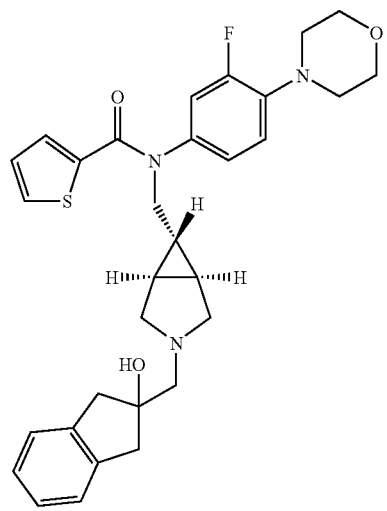

Exo-N-{3-[6-ethyl-3-(2-hydroxy-indan-2-ylmethyl)-3-aza-bicyclo[3.1.0]hex-6-yl]-phenyl}-(2-methoxyethane)sulfonamide:

Following General Method B, Exo-N-{3-[6-ethyl-3-aza-bicyclo[3.1.0]hex-6-yl]-phenyl}-(2-methoxyethane)sulfonamide trifluoroacetate (5.4 g, 12 mmol) and hydroxy-(2-hydroxyindan-2-yl)-methanesulfonic acid, sodium salt (8.2 g, 31 mmol) were coupled to provide the title compound.

EXAMPLE 7

Thiophene-2-carboxylic acid (3-fluoro-4-morpholin-4-yl-phenyl)-[Exo-3-(2-hydroxy-indan-2-ylmethyl)-3-aza-bicyclo[3.1.0]hex-6-ylmethyl]-amide:

Following General Method B, Thiophene-2-carboxylic acid (3-fluoro-4-morpholin-4-yl-phenyl)-[Exo-3-aza-bicyclo[3.1.0]hex-6-ylmethyl]-amide (100 mg, 0.25 mmol) and hydroxy-(2-hydroxyindan-2-yl)-methanesulfonic acid, sodium salt (166 mg, 0.62 mmol) were coupled to provide the title compound.

EXAMPLE 8

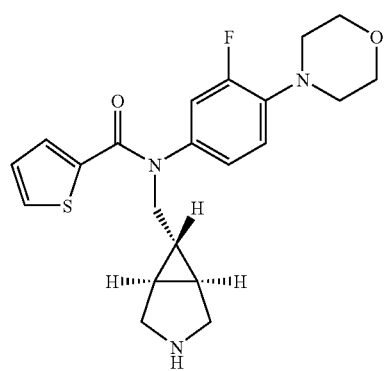

+

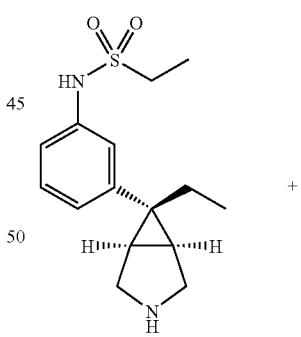

+

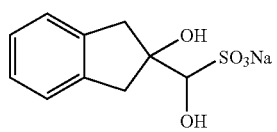  →

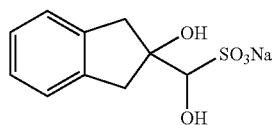  →

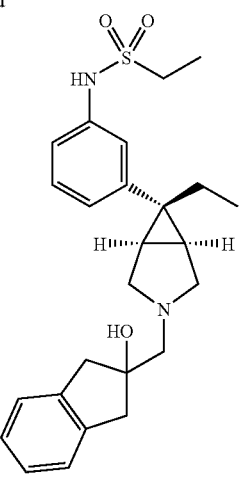

Exo-N-{3-[6-ethyl-3-(2-hydroxy-indan-2-ylmethyl)-3-aza-bicyclo[3.1.0]hex-6-yl]-phenyl}-ethanesulfonamide:

Following General Method B, Exo-N-{3-[6-ethyl-3-aza-bicyclo[3.1.0]hex-6-yl]-phenyl}-ethanesulfonamide (400 mg, 1.36 mmol) and hydroxy-(2-hydroxyindan-2-yl)-methanesulfonic acid, sodium salt (907 mg, 3.40 mmol) were coupled to provide the title compound.

EXAMPLE 9

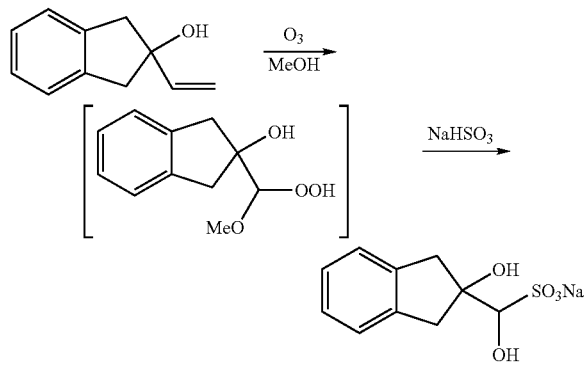

Bisulfite Adduct Formation, General Method C: Sodium hydroxy-(2-hydroxyindan-2-yl)-methanesulfonate (The following representative procedure is taken from Ragan et al., *Org. Process Res. Dev.* 2003, 7, 155–160). 2-Vinyl-indan-2-ol (15.0 g, 93.6 mmol) was dissolved in 150 mL MeOH, cooled to −78° C., and treated with a stream of ozone generated from $O_2$. The dark solution became lighter in color after ca. 15 min, and HPLC analysis indicated consumption of starting material. Oxygen was bubbled through the solution for 5 min, then a stream of nitrogen was bubbled through for 30 min. A slurry of $NaHSO_3$ (19.5 g, 187 mmol) in 15 mL water was then added, and the mixture was allowed to gradually warm to room temperature. After 30 min, a starch-KI strip tested negative for peroxides. The slurry was then heated to 60° C. for 30 min to complete formation of the bisulfite adduct. After cooling to room temperature and stirring for 2 h, the resulting solids were collected and rinsed with methanol (2×30 mL), to provide the desired product as a while powder (16.2 g, 61% yield from 2-indanone). Combustion analysis of this material indicated 56% purity (Anal. Calcd for $C_{10}H_{11}SO_5Na$: C, 45.1; H, 4.2. Found: C, 25.2; H, 2.6). Recrystallization from 10 volumes of water provided analytically pure material in 47% recovery (8.01 g recrystallized from 80 mL water, isolated 3.75 g analytically pure 2):

EXAMPLE 10

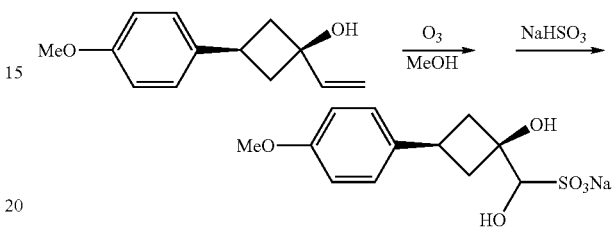

Hydroxy-[cis-1-hydroxy-3-(4-methoxy-phenyl)-cyclobutyl]-methanesulfonic acid, sodium salt:

Following General Procedure C, cis-3-(4-methoxy-phenyl)-1-vinyl-cyclobutanol was converted into the title compound.

EXAMPLE 11

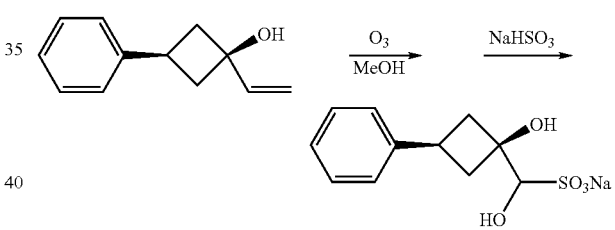

Hydroxy-[cis-1-hydroxy-3-phenyl-cyclobutyl]-methanesulfonic acid, sodium salt:

Following General Procedure C, cis-3-phenyl-1-vinyl-cyclobutanol was converted into the title compound.

EXAMPLE 12

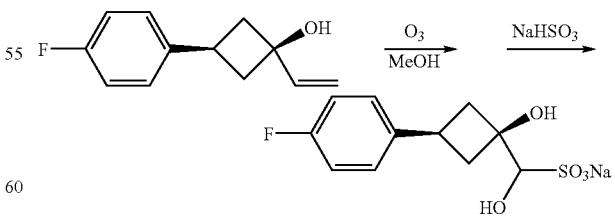

Hydroxy-[cis-1-hydroxy-3-(4-fluoro-phenyl)-cyclobutyl]-methanesulfonic acid, sodium salt:

Following General Procedure C, cis-3-(4-fluoro-phenyl)-1-vinyl-cyclobutanol was converted into the title compound.

EXAMPLE 13

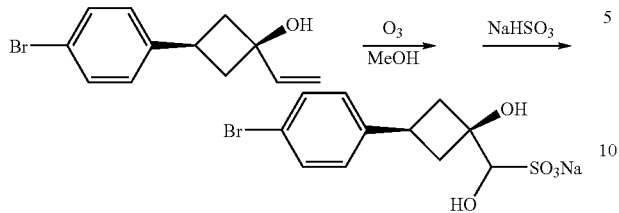

Hydroxy-[cis-1-hydroxy-3-(4-bromo-phenyl)-cyclobutyl]-methanesulfonic acid, sodium salt:

Following General Procedure C, cis-3-(4-bromo-phenyl)-1-vinyl-cyclobutanol was converted into the title compound.

The invention claimed is:

1. A process for preparing a compound of formula

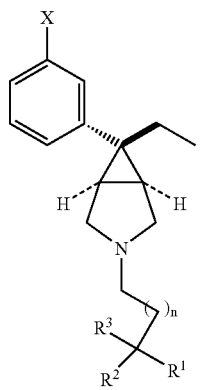

I wherein X is halogen, —OH, —CN, —$C_1$ to $C_4$ alkyl substituted with one to three halogen atom, —$NH_2$, —NH($C_1$–$C_4$ alkyl), —N($C_1$–$C_4$ alkyl)($C_1$–$C_4$ alkyl), —C(=O)$NH_2$, —C(=O)NH($C_1$–$C_4$alkyl), —C(=O)N($C_1$–$C_4$ alkyl)($C_1$–$C_4$ alkyl), —NHS(=O)$_2$H, or —NHS(=O)$_2R^4$;

$R^1$ and $R^2$ are, with the carbon to which they are attached, connected to form a $C_3$–$C_7$ cycloalkyl or a 4–7 membered heterocycloalkyl comprising from one to three hetero moieties selected from O, S, —C(=O), and N; and wherein said cycloalkyl or heterocycloalkyl optionally contains one or two double bonds; and wherein said cycloalkyl or heterocycloalkyl is optionally fused or attached to a $C_6$–$C_{14}$ aryl or 5–14 membered heteroaryl group;

$R^3$ is $C_1$–$C_4$ alkyl which may optionally contain one or two unsaturated bonds, —OH, —CN, —$NO_2$, —O$C_1$–$C_4$ alkyl, —$NH_2$ amide or alkyl substituted amide;

and n is one or zero;

$R^4$ is selected from $C_1$–$C_4$ alkyl, -($C_1$–$C_4$ alkylene)—O—($C_1$–$C_4$ alkyl), 4-(1-methylimidazole), -($C_1$–$C_4$ alkylene)—$NH_2$, -($C_1$–$C_4$ alkylene)—NH($C_1$–$C_4$ alkyl), -($C_1$–$C_4$ alkylene)—N($C_1$–$C_4$ alkyl)($C_1$–$C_4$ alkyl);

comprising reacting a compound of formula

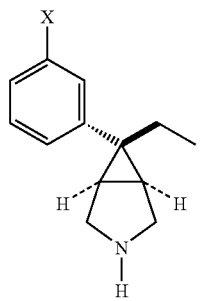

II with a compound of formula

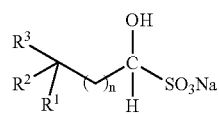

III in the presence of a reducing agent and an organic solvent.

2. A process according to claim 1 wherein $R^1$ and $R^2$ are, with the carbon to which they are attached, connected to form a $C_5$ cycloalkyl group.

3. A process according to claim 1 wherein said reducing agent is sodium triacetoxyborohydride.

4. A process according to claim 1 wherein said organic solvent is a mixture comprising NMP and cyclohexane.

5. A process according to claim 1 wherein said compound of formula III is the addition product of aqueous sodium bisulfite and an organic aldehyde of formula IV.

6. A process according to claim 5, wherein the aldehyde-bisulfite adduct (III) exists in solution equilibrium with sodium bisulfite and the corresponding aldehyde.

7. A process according to claim 5, wherein the aldehyde-bisulfite adduct (III) in the presence of a base is substantially dissociated into sodium bisulfite and the corresponding aldehyde (IV).

8. A process according to claim 1, wherein the compound of formula III is selected from the group consisting of
Hydroxy-(2-hydroxyindan-2-yl)-methanesulfonic acid, sodium salt;
Hydroxy-[cis-1-hydroxy-3-(4-methoxy-phenyl)-cyclobutyl]-methanesulfonic acid, sodium salt;
Hydroxy-[cis-1-hydroxy-3-phenyl-cyclobutyl]-methanesulfonic acid, sodium salt;
Hydroxy-[cis-1-hydroxy-3-(4-fluoro-phenyl)-cyclobutyl]-methanesulfonic acid, sodium salt; and
Hydroxy-[cis-1-hydroxy-3-(4-bromo-phenyl)-cyclobutyl]-methanesulfonic acid, sodium salt.

9. A process according to claim 1, wherein the compound of formula 1 is selected from the group consisting of
Exo-N-{3-[6-ethyl-3-(2-hydroxy-indan-2-ylmethyl)-3-aza-bicyclo[3.1.0]hex-6-yl]-phenyl}methanesulfonamide;
Exo-{3-[6-ethyl-3-(cis-1-hydroxy-3-phenyl-cyclobutylmethyl)-3-aza-bicyclo[3.1.0]hex-6-yl]-phenyl}-propanesulfonamide;
Exo-N-{3-[6-ethyl-3-(2-hydroxy-indan-2-ylmethyl)-3-aza-bicyclo[3.1.0]hex-6-yl]-phenyl}propanesulfonamide;

Exo-{3-[6-ethyl-3-(cis-1-hydroxy-3-(4-bromo-phenyl)-cyclobutylmethyl)-3-aza-bicyclo[3.1.0]hex-6-yl]-phenyl}-methanesulfonamide;

Exo-N-{3-[6-ethyl-3-(2-hydroxy-indan-2-ylmethyl)-3-aza-bicyclo[3.1.0]hex-6-yl]-phenyl}-(2-methoxyethane)sulfonamide;

Thiophene-2-carboxylic acid (3-fluoro-4-morpholin-4-yl-phenyl)-[Exo-3-(2-hydroxy-indan-2-ylmethyl)-3-aza-bicyclo[3.1.0]hex-6-ylmethyl]-amide; and Exo-N-{3-[6-ethyl-3-(2-hydroxy-indan-2-ylmethyl)-3-aza-bicyclo[3.1.0]hex-6-yl]-phenyl}-ethanesulfonamide;

and their pharmaceutically acceptable salts and prodrugs.

10. A process according to claim 7 wherein the organic solvent is 2-methyl-tetrahydrofuran and sufficient aqueous sodium hydroxide is present to elevate the pH of the reaction mixture to a pH greater than 9.0.

11. A process according to claim 1 wherein n is zero and $R^3$ is hydroxyl.

* * * * *